United States Patent
Ries et al.

(10) Patent No.: US 9,403,022 B2
(45) Date of Patent: Aug. 2, 2016

(54) HEADER ASSEMBLY FOR IMPLANTABLE MEDICAL DEVICE

(75) Inventors: Andrew J. Ries, Lino Lakes, MN (US); David B. Engmark, Bethel, MN (US); John E. Kast, Hugo, MN (US); Jean-Francois Fischer, Etoy (CH)

(73) Assignee: Medtronic, Inc., Minneapolis, MN (US)

( * ) Notice: Subject to any disclaimer, the term of this patent is extended or adjusted under 35 U.S.C. 154(b) by 952 days.

(21) Appl. No.: 12/696,931

(22) Filed: Jan. 29, 2010

(65) Prior Publication Data
US 2011/0190833 A1  Aug. 4, 2011

(51) Int. Cl.
*A61N 1/375* (2006.01)
*H01R 13/52* (2006.01)
*A61N 1/36* (2006.01)

(52) U.S. Cl.
CPC .............. *A61N 1/375* (2013.01); *A61N 1/3605* (2013.01); *A61N 1/3754* (2013.01); *H01R 13/5224* (2013.01); *Y10T 29/49002* (2015.01)

(58) Field of Classification Search
CPC ... A61N 1/375; A61N 1/3754; A61N 1/3752; Y10T 29/49002; Y10T 29/49174; H01R 13/5224
USPC ..................................................... 607/36, 37
See application file for complete search history.

(56) References Cited

U.S. PATENT DOCUMENTS

| | | |
|---|---|---|
| 4,262,673 A | 4/1981 | Kinney et al. |
| 4,355,646 A | 10/1982 | Kallok et al. |
| 4,381,014 A | 4/1983 | Sandstrom et al. |
| 4,469,104 A | 9/1984 | Peers-Trevarton |
| 4,707,566 A | 11/1987 | Titcombe et al. |
| 4,712,557 A | 12/1987 | Harris |
| 4,869,255 A | 9/1989 | Putz |
| 4,934,366 A | 6/1990 | Truex et al. |
| 5,046,242 A | 9/1991 | Kuzma |
| 5,076,270 A | 12/1991 | Stutz, Jr. |
| 5,336,246 A * | 8/1994 | Dantanarayana ............... 607/37 |
| 5,354,326 A | 10/1994 | Comben et al. |
| 5,411,348 A | 5/1995 | Balsells |
| 5,474,309 A | 12/1995 | Balsells |
| 5,503,375 A | 4/1996 | Balsells |
| 5,532,436 A | 7/1996 | Moyers et al. |
| 5,545,842 A | 8/1996 | Balsells |

(Continued)

FOREIGN PATENT DOCUMENTS

| | | |
|---|---|---|
| WO | 9848896 A1 | 11/1998 |
| WO | 2007109762 A1 | 9/2007 |
| WO | 2009045809 A2 | 4/2009 |

OTHER PUBLICATIONS (PCT/US2001/021228) PCT Notification of Transmittal of the International Search Report and the Written Opinion of the International Searching Authority, 9 pages.

*Primary Examiner* — Tammie K Heller

(57) ABSTRACT

An implantable medical device includes a housing; at least one module enclosed within the housing and configured to at least one of generate an electrical stimulation therapy for delivery to a patient or monitor a physiological parameter of the patient; one or more feedthroughs extending through the housing; a header assembly including one or more electrical connectors electrically coupled to the module via the feedthroughs; and a preformed gasket compressed between the housing and the header assembly forming a seal to electrically isolate the feedthroughs from an external environment.

30 Claims, 6 Drawing Sheets

(56) References Cited

U.S. PATENT DOCUMENTS

| | | | |
|---|---|---|---|
| 5,560,358 A | 10/1996 | Arnold et al. | |
| 5,575,487 A | 11/1996 | Balsells | |
| 5,584,873 A | 12/1996 | Shoberg et al. | |
| 5,599,027 A | 2/1997 | Balsells | |
| 5,615,870 A | 4/1997 | Balsells | |
| 5,620,476 A | 4/1997 | Truex et al. | |
| 5,709,371 A | 1/1998 | Balsells | |
| 5,791,638 A | 8/1998 | Balsells | |
| 5,851,221 A | 12/1998 | Rieder et al. | |
| 5,871,514 A | 2/1999 | Wiklund et al. | |
| 5,871,515 A * | 2/1999 | Wiklund et al. | 607/36 |
| 5,947,761 A | 9/1999 | Pepe | |
| 5,979,904 A | 11/1999 | Balsells | |
| 5,984,316 A | 11/1999 | Balsells | |
| 5,992,856 A | 11/1999 | Balsells et al. | |
| 6,006,135 A | 12/1999 | Kast et al. | |
| 6,050,572 A | 4/2000 | Balsells et al. | |
| 6,064,509 A | 5/2000 | Tonar et al. | |
| 6,161,838 A | 12/2000 | Balsells | |
| 6,162,101 A | 12/2000 | Fischer et al. | |
| 6,264,205 B1 | 7/2001 | Balsells | |
| 6,321,126 B1 | 11/2001 | Kuzma | |
| 6,415,168 B1 | 7/2002 | Putz | |
| 6,575,793 B1 | 6/2003 | Li et al. | |
| 6,662,035 B2 | 12/2003 | Sochor | |
| 6,671,534 B2 | 12/2003 | Putz | |
| 6,725,096 B2 | 4/2004 | Chinn et al. | |
| 6,741,892 B1 | 5/2004 | Meadows et al. | |
| 6,776,635 B2 | 8/2004 | Blanchfield et al. | |
| 6,884,122 B2 | 4/2005 | Robison et al. | |
| 7,083,474 B1 | 8/2006 | Fleck et al. | |
| 7,110,827 B2 | 9/2006 | Sage et al. | |
| 7,134,919 B2 | 11/2006 | Putz | |
| 7,167,749 B2 | 1/2007 | Biggs et al. | |
| 7,274,963 B2 | 9/2007 | Spadgenske | |
| 7,402,083 B2 | 7/2008 | Kast et al. | |
| 7,425,142 B1 | 9/2008 | Putz | |
| 7,425,145 B2 | 9/2008 | Ngo | |
| 7,537,493 B2 | 5/2009 | Ries et al. | |
| 7,731,550 B2 | 6/2010 | Falchetti | |
| 7,798,862 B2 | 9/2010 | Kast et al. | |
| 7,892,050 B2 | 2/2011 | Pavlovic et al. | |
| 8,103,348 B1 | 1/2012 | Coffed et al. | |
| 2002/0099430 A1 | 7/2002 | Verness | |
| 2002/0115343 A1 | 8/2002 | Sommer et al. | |
| 2002/0193859 A1 | 12/2002 | Schulman et al. | |
| 2003/0050549 A1 | 3/2003 | Sochor | |
| 2003/0069612 A1 | 4/2003 | Zart et al. | |
| 2003/0082958 A1 | 5/2003 | Robinson et al. | |
| 2003/0163171 A1 | 8/2003 | Kast et al. | |
| 2004/0093038 A1 | 5/2004 | Biggs et al. | |
| 2004/0215303 A1 | 10/2004 | Sage | |
| 2005/0033138 A1 | 2/2005 | Ries et al. | |
| 2005/0118887 A1 | 6/2005 | Hoffer et al. | |
| 2006/0122658 A1 | 6/2006 | Kronich et al. | |
| 2006/0167522 A1 | 7/2006 | Malinowki | |
| 2007/0150020 A1 | 6/2007 | Hokanson et al. | |
| 2007/0239222 A1 | 10/2007 | Sprain et al. | |
| 2010/0240253 A1 | 9/2010 | Kast et al. | |
| 2010/0256695 A1 | 10/2010 | Iyer et al. | |
| 2010/0304592 A1 * | 12/2010 | Kast et al. | 439/271 |
| 2011/0106189 A1 | 5/2011 | Seeley et al. | |
| 2011/0137414 A1 | 6/2011 | Litzke et al. | |

* cited by examiner

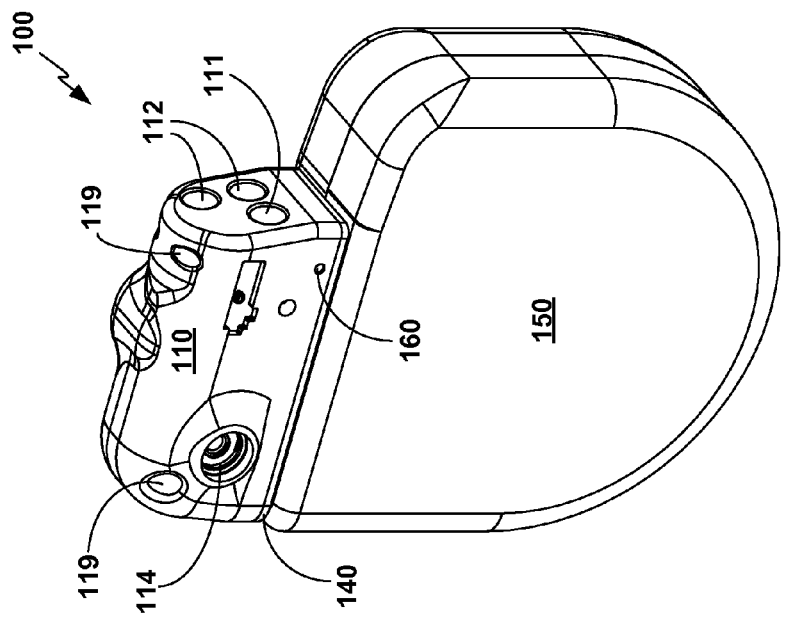
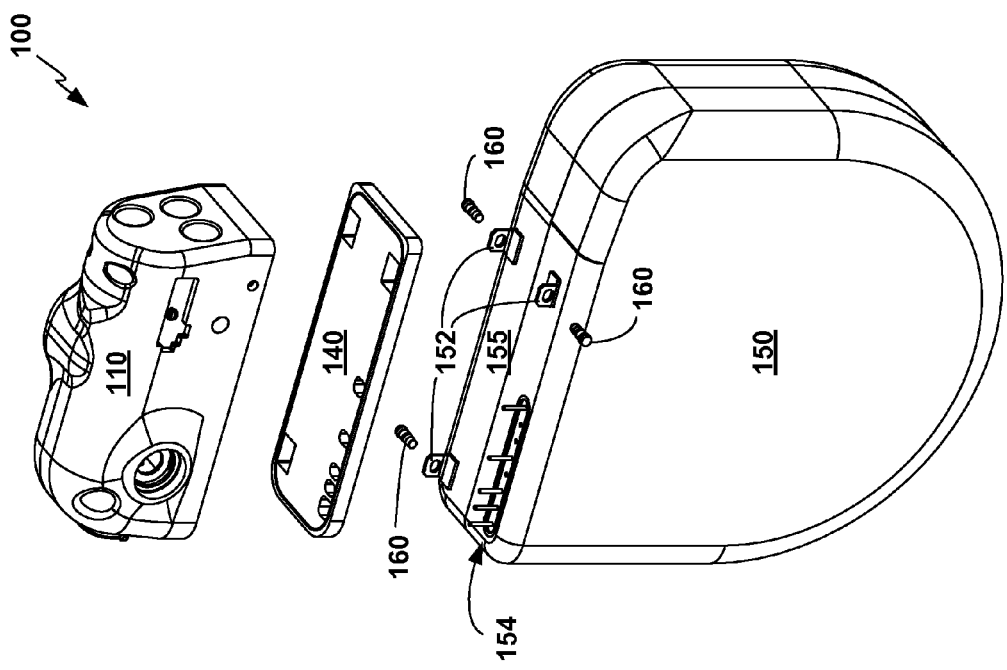

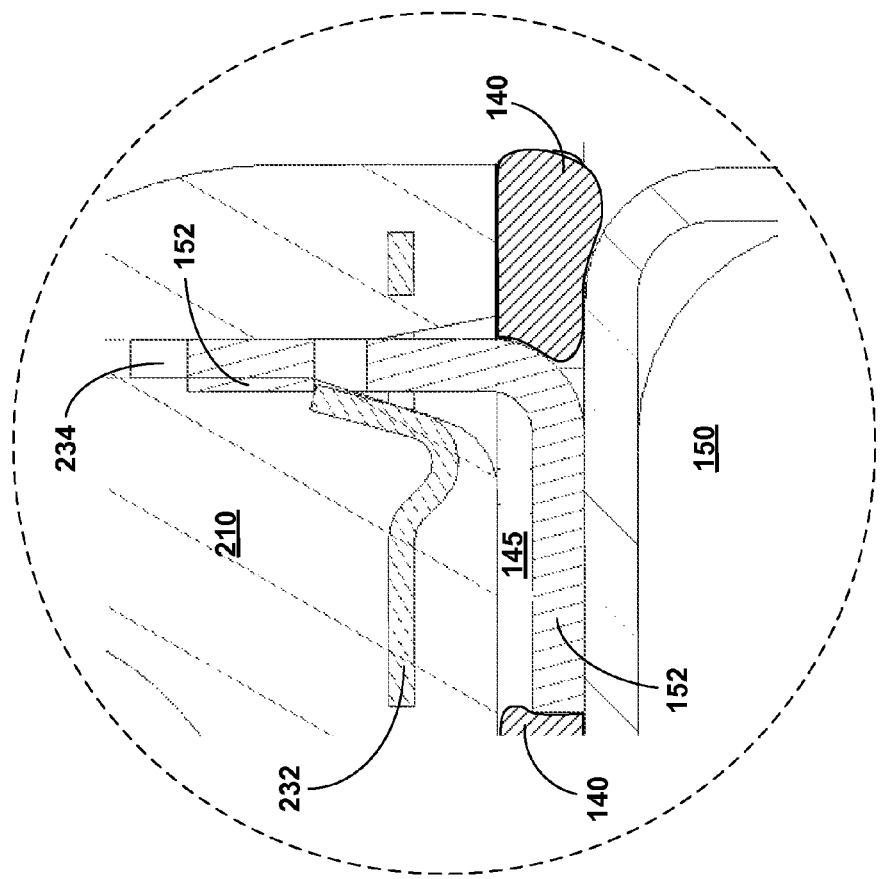
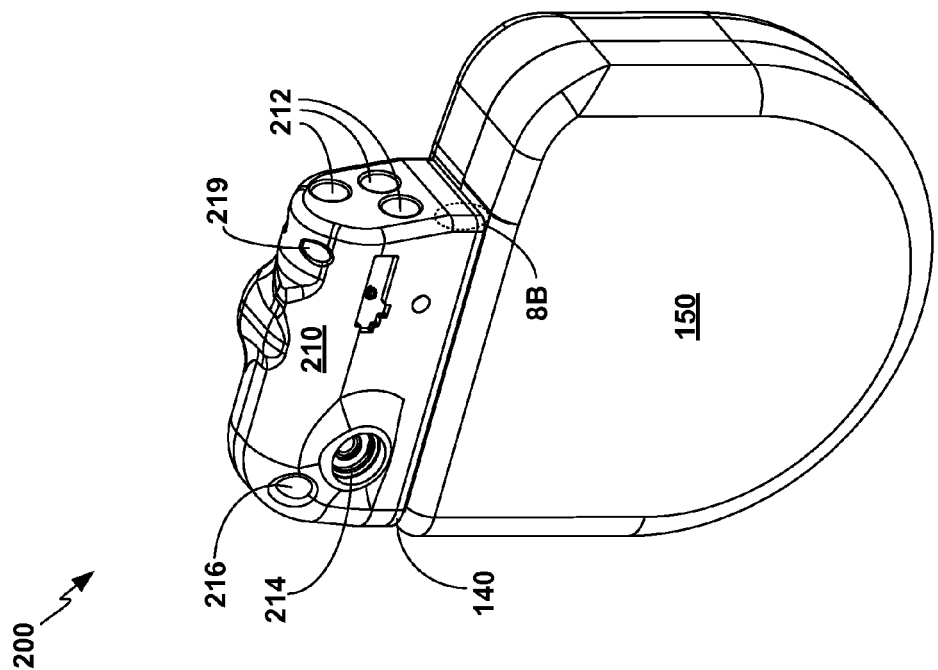
FIG. 8B
FIG. 8A

HEADER ASSEMBLY FOR IMPLANTABLE MEDICAL DEVICE

TECHNICAL FIELD

The disclosure relates to implantable medical devices.

BACKGROUND

A wide variety of implantable medical devices that deliver a therapy or monitor a physiologic condition of a patient have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, at least some of which may be included as part of one or more elongated implantable medical leads. Implantable medical leads may be configured to allow electrodes or sensors to be positioned at desired locations for delivery of stimulation or sensing electrical depolarizations. For example, electrodes or sensors may be located at a distal portion of the lead. A proximal portion of the lead may be coupled to an implantable medical device housing, which may contain electronic circuitry such as stimulation generation and/or sensing circuitry. In some cases, electrodes or sensors may be positioned on an IMD housing as an alternative or in addition to electrodes or sensors deployed on one or more leads.

Implantable cardiac devices, such as cardiac pacemakers or implantable cardioverter defibrillators, provide therapeutic electrical stimulation to the heart by delivering electrical therapy signals such as pulses or shocks for pacing, cardioversion, or defibrillation via electrodes of one or more implantable leads. In some cases, an implantable cardiac device may sense intrinsic depolarizations of the heart, and control the delivery of therapeutic stimulation to the heart based on the sensing. When an abnormal rhythm of the heart is detected, such as bradycardia, tachycardia or fibrillation, an appropriate electrical therapy (e.g., in the form of pulses) may be delivered to restore the normal rhythm. For example, in some cases, an implantable medical device may deliver pacing, cardioversion or defibrillation signals to the heart of the patient upon detecting ventricular tachycardia, and deliver defibrillation therapy to a patient's heart upon detecting ventricular fibrillation.

SUMMARY

In general, the disclosure is directed to techniques for securing and electrically sealing header assemblies of implantable medical devices (IMDs) to IMD housings without using a wet adhesive or back filling. Once type of header assembly is a lead connector assembly. As an example, an IMD may include feedthroughs that pass through an IMD housing to electrically connect a lead connector assembly to electrical components within an enclosure formed by the IMD housing. The IMD may further include a preformed gasket between the lead connector assembly and the housing of the IMD. The lead connector assembly may be mechanically secured to the housing such that the preformed gasket is compressed between the lead connector assembly and the housing to form a seal that electrically isolates feedthroughs from each other.

In one example, this disclosure is directed to an implantable medical device comprising: a housing; a module enclosed within the housing and configured to at least one of generate an electrical stimulation therapy for delivery to a patient or monitor a physiological parameter of the patient; one or more feedthroughs extending through the housing; a header assembly including one or more electrical connectors electrically coupled to the module via the feedthroughs; and a preformed gasket compressed between the housing and the header assembly forming a seal to electrically isolate the feedthroughs from an external environment.

In another example, this disclosure is directed to a method of manufacturing an implantable medical device. The method comprises obtaining a subassembly. The subassembly includes a substantially sealed housing, a module enclosed within the housing and configured to at least one of generate an electrical stimulation therapy for delivery to a patient or monitor a physiological parameter of the patient, and one or more feedthroughs extending through the housing. The method further comprises obtaining a header assembly including one or more electrical connectors, and obtaining a preformed gasket configured to electrically isolate the feedthroughs from an external environment when the header assembly is mounted to the substantially sealed housing. The method further comprises positioning the preformed gasket between the header assembly and the housing, positioning the header assembly on the housing to form one or more electrical connections between the feedthroughs and the electrical connectors and compress the preformed gasket between the header assembly and the housing to form a seal that electrically isolates the feedthroughs from the external environment; and mechanically securing the header assembly to the housing to maintain the seal provided by the preformed gasket.

In another example, this disclosure is directed to an implantable medical device comprising: a housing; a module enclosed within the housing and configured to at least one of generate an electrical stimulation therapy for delivery to a patient or monitor a physiological parameter of the patient; one or more feedthroughs extending through the housing; a header assembly including an electrical connector electrically coupled to the module via the feedthroughs; and means for electrically isolating the feedthroughs from an external environment.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIGS. 3A-3B illustrate an IMD with an example medical lead connector assembly and an example preformed gasket.

FIGS. 8A-8B illustrate an IMD with an example medical lead connector assembly.

DETAILED DESCRIPTION

Figure 1:
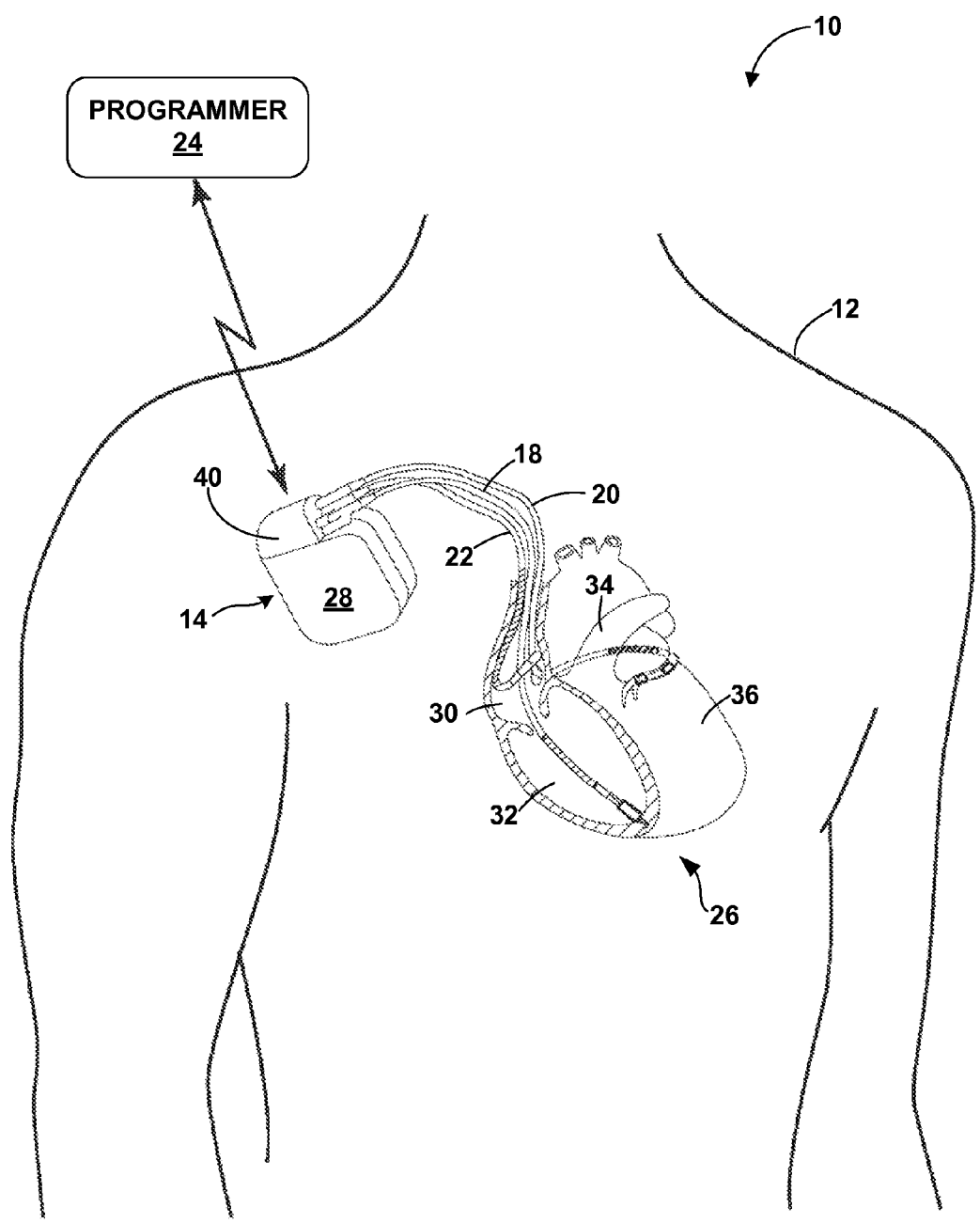
FIG. 1 is a conceptual diagram illustrating an example system that includes an implantable medical device (IMD) configured to deliver electrical stimulation to and/or monitor a patient.

FIG. 1 is a conceptual diagram illustrating an example system 10 that provides therapy to and/or monitors patient 12. System 10 includes implantable medical device (IMD) 14 and leads 18, 20, 22, and programmer 24. As described in greater detail below, leads 18, 20, 22 are mechanically and electrically coupled to IMD 14 via a header assembly, which may be connected housing 28 of IMD 14 as shown in FIG. 1. In the example of FIG. 1, the header assembly comprises a lead connector assembly 40 that connects to leads 18, 20, 22 to IMD 14. Housing 28 and lead connector assembly 40 are separate components that are mechanically coupled together, e.g., via bracket and pin connections or snap-on connections. As discussed in further detail below, IMD 14 may include a preformed gasket (not shown in FIG. 1) between housing 28 and lead connector assembly 40 that electrically isolates feedthroughs that extend from housing 28 into lead connector assembly 40 from each other. In the example shown in FIG. 1, housing 28 and lead connector assembly 40 can be fabricated from any suitable biocompatible material or combination of biocompatible materials, such as, but not limited to, stainless steel or titanium. Housing 28 and lead connector assembly 40 may be formed from the same material or materials, or different materials.

In some examples, IMD 14 generates and delivers electrical stimulation to heart 26 via electrodes carried by one or more of leads 18, 20, 22 in order to manage a cardiac rhythm of heart 26. In such examples, IMD 14 includes a therapy module that generates at least one of pacing, cardioversion, defibrillation or cardiac resynchronization therapy. The pacing therapy may include, for example, antitachyarrhythmia pacing (ATP) and pacing therapies designed to prevent ventricular tachycardia, ventricular fibrillation, atrial tachycardia, and/or atrial fibrillation, or cardiac resynchronization therapy (CRT). In some examples, IMD 14 provides pacing, but not cardioversion or defibrillation, while in other examples, IMD 14 provides cardioversion or defibrillation, but not pacing. In addition, in further examples, IMD 14 provides pacing, cardioversion, and defibrillation. Alternatively, or in addition to, the therapy module, IMD 14 may include a sensing module. The sensing module may sense one or more physiological conditions of a patient such as electrical depolarization/repolarization signals from heart 26 (referred to as "electrogram" or EGM), intracardiac or intravascular pressure, activity, posture, respiration, or thoracic impedance. In other examples, an IMD may include more or less than three leads for delivering therapy and or sensing.

In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 26. Right atrial (RA) lead 22 extends through one or more veins and the vena cava, and into the right atrium 30 of heart 26. In other examples, IMD 14 delivers stimulation therapy to heart 26 by delivering stimulation to an extravascular tissue site in addition to or instead of delivering stimulation via electrodes of intravascular leads 18, 20, 22. An extravascular tissue site is outside of heart 26 and outside of arteries, veins, or other vasculature of patient 12.

IMD 14 may sense electrical signals attendant to the depolarization and repolarization of heart 26 via electrodes (not shown in FIG. 1) coupled to at least one of the leads 18, 20, 22. In some examples, IMD 14 provides pacing pulses to heart 26 based on the electrical signals sensed within heart 26. The configurations of electrodes used by IMD 14 for sensing and pacing may be unipolar or bipolar. IMD 14 may also provide defibrillation therapy and/or cardioversion therapy via electrodes located on at least one of the leads 18, 20, 22. IMD 14 may detect arrhythmia of heart 26, such as fibrillation of ventricles 32 and 36, and IMD 14 may be programmed to deliver a progression of therapies, e.g., pulses with increasing energy levels, until a fibrillation of heart 26 is stopped. IMD 14 may detect fibrillation employing one or more fibrillation detection techniques known in the art.

In some examples, IMD 14 may also be referred to as a signal generator, stimulation generator or an electrical stimulator. In some examples, lead 16 may also carry one or more sense electrodes to permit IMD 14 to sense electrical signals within patient 12. In some examples, the same electrodes may be used for sensing and for stimulation.

In the example of FIG. 1, IMD 14 has been implanted in patient 12 at a location that allows leads 18, 20, 22 to be positioned within heart 26. For example, IMD 14 may be subcutaneously or submuscularly implanted in the body of a patient 12 (e.g., in a chest cavity, lower back, lower abdomen, or buttocks of patient 12).

In the example shown in FIG. 1, IMD 14 provides cardiac rhythm therapy. Accordingly, the components for generating and delivering the pacing, cardioversion and/or defibrillation therapy via leads 18, 20, and 22 may be substantially contained within outer housing 28 of IMD 14. As described in further detail below, lead connector assembly 40 includes electrical connectors that respectively mechanically couple leads 18, 20, 22 to IMD 14 and electrically connect leads 18, 20, 22 to a therapy or sensing module within housing 28. For example, a proximal end of each of leads 16, 18, 20, may be both electrically and mechanically coupled to lead connector assembly 40 of IMD 14 either directly or indirectly (e.g., via a lead extension). Electrical conductors disposed in the respective lead body may electrically connect stimulation electrodes (and sense electrodes, if present) of leads 18, 20, 22 to the therapy and/or sensing modules within IMD 14 via lead connector assembly 40. Lead connector assembly 40 may also be referred to as a header assembly or a connector block.

While the disclosure primarily describes leads as being directly connected to lead connector assembly 40, in other examples, leads, such as leads 18, 20, 22, may be indirectly mechanically and electrically connected to lead connector assembly 40 via one or more lead extensions. A lead extension may effectively elongate a lead. In addition, in some examples, a bifurcated or trifurcated lead extension may be useful for mechanically and electrically connecting more than one lead to a common electrical connector of lead connector assembly 40.

In some examples, IMD 14 also includes one or more housing electrodes, which may be formed integrally with an outer surface of hermetically-sealed housing 28 of IMD 14 or otherwise coupled to housing 28. In some examples, the housing electrode may be defined by an uninsulated portion of an outward facing portion of housing 28. Other divisions between insulated and uninsulated portions of housing 28 may be employed to define two or more housing electrodes. In some examples, such as the example shown in FIG. 1, the housing electrode may comprise substantially all of housing 28. In other examples, one or more electrodes may be embedded into an insulating casing that surrounds the outer surface of housing 28 or otherwise attached to outer housing 28 of IMD 14. Any of the electrodes of leads 18, 20, 22 may be used for unipolar sensing or stimulation in combination with the one or more housing electrodes.

In some examples, IMD 14 includes one or more header assembly electrodes in addition to or instead of electrodes of leads 18, 20 and 22. The header assembly electrodes may be formed integrally with an outer surface of the header assembly, such as the outer surface of lead connector assembly 40 of IMD 14. In some examples, the header assembly electrode may be defined by an uninsulated portion of an outward facing portion of the header assembly. Other divisions between insulated and uninsulated portions of the header assembly may be employed to define two or more header assembly electrodes. In some examples, such as the example shown in FIG. 1, the header assembly electrode may comprise substantially all of lead connector 40. In other examples, one or more electrodes may be embedded into an insulating casing that surrounds the outer surface of lead connector 40 or otherwise attached to lead connector 40. In further examples, the header assembly may not connect to any leads. In this case, a plurality of header assembly electrodes, housing electrodes or both may be used to monitor one or more parameters of patient 12. The header assembly may also include one or more feedthroughs via which other conductive components (e.g., antenna) within the header assembly couple to electronic components within housing 28 of IMD 14 (e.g., transceiver).

As shown in FIG. 1, system 10 also includes programmer 24. In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display.

A user, such as a physician, technician, or other clinician, may interact with programmer 24 to communicate with IMD 14. For example, the user may interact with programmer 24 to retrieve physiological or diagnostic information from IMD 14. A user may also interact with programmer 24 to program IMD 14, e.g., select values for operational parameters for one or more of the stimulation therapies delivered by IMD 14. For example, the user may use programmer 24 to retrieve information from IMD 14 regarding the rhythm of heart 26, trends therein over time, or tachyarrhythmia episodes. As another example, the user may use programmer 24 to retrieve information from IMD 14 regarding other sensed physiological parameters of patient 12, such as electrical depolarization/repolarization signals from heart 26 (referred to as "electrogram" or EGM), intracardiac or intravascular pressure, activity, posture, respiration, or thoracic impedance. As another example, the user may use programmer 24 to retrieve information from IMD 14 regarding the performance or integrity of IMD 14 or other components of system 10 corresponding to the first stimulation therapy, such as leads 18, 20, and 22, or a power source of IMD 14.

The user may use programmer 24 to program a therapy progression, select electrodes used to deliver defibrillation pulses, select waveforms for the defibrillation pulse, or select or configure a fibrillation detection algorithm for IMD 14. The user may also use programmer 24 to program aspects of other therapies provided by IMD 14, such as cardioversion, pacing or other electrical stimulation therapies. For example, with the aid of programmer 24, a user may select therapy parameters for the pacing, cardioversion, and/or defibrillation therapy delivered by leads 18, 20, 22.

Programmer 24 may communicate with IMD 14 via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 14 implant site in order to improve the quality or security of communication between IMD 14 and programmer 24.

Figure 2:
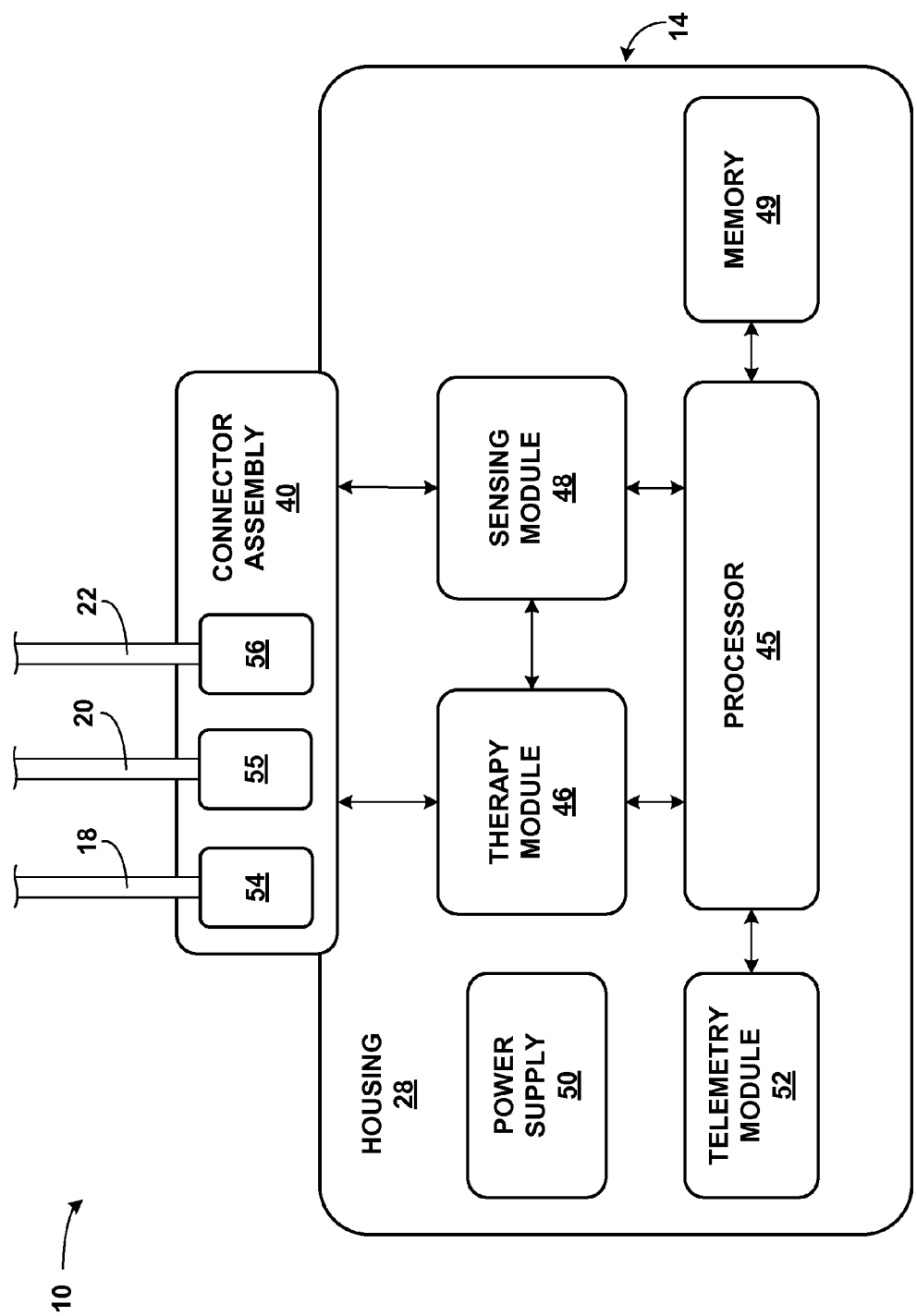
FIG. 2 is a functional block diagram illustrating the IMD of FIG. 1.

FIG. 2 is a functional block diagram illustrating example system 10 including IMD 14, lead connector assembly 40 and leads 18, 20, 22. As shown in FIG. 2, IMD 14 includes processor 45, therapy module 46, sensing module 48, memory 49, power supply 50, and telemetry module 52. Memory 49 may include computer-readable instructions that, when executed by processor 45, cause processor 45 to perform various functions attributed to processor herein. Memory 49 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 45 may include any one or more of a microprocessor, a controller, a digital signal processor (DSP), an application specific integrated circuit (ASIC), a field-programmable gate array (FPGA), or equivalent discrete or integrated logic circuitry. In some examples, processor 45 may include multiple components, such as any combination of one or more microprocessors, one or more controllers, one or more DSPs, one or more ASICs, or one or more FPGAs, as well as other discrete or integrated logic circuitry. The functions attributed to processor 45 herein may be embodied as software, firmware, hardware or any combination thereof. Processor 45 may control modules 46, 48, respectively, to generate and deliver therapy to patient 12 and/or sense one or more physiological conditions of a patient according to one or more control programs, which may be stored in memory 49.

Therapy module 46 includes a signal generator to generate the stimulation signals for delivery to patient 12. Therapy module 46 may be configured generate and deliver electrical stimulation signals including at least one of pacing, cardioversion or defibrillation therapy to heart 26 of patient 12 via leads 18, 20, 22. If therapy module 46 is configured to generate and deliver defibrillation pulses to heart 26, therapy module 46 may include a high voltage charge circuit and a high voltage output circuit. If therapy module 46 is configured to generate and deliver pacing pulses to heart 26, processor 45 may include pacer timing and control module, which may be embodied as hardware, firmware, software, or any combination thereof. The pacer timing and control module may comprise a dedicated hardware circuit, such as an ASIC, separate from other processor 45 components, such as a microprocessor, or a software module executed by a component of processor 45, which may be a microprocessor or ASIC. The pacer timing and control module may be used by processor 45 to time the delivery of pacing pulses to heart 26.

Sensing module 48 monitors signals from at least one of the electrodes of leads 18, 20, 22, the header assembly and/or housing 28 in order to monitor electrical activity of heart 26, e.g., via an EGM signal. In some examples, sensing module 48 may include one or more sensing channels, each of which may comprise an amplifier. Under the control of processor 45, the switch module of sensing module 48 may couple the outputs from the selected electrodes to one of the sensing channels. The sensed electrical activity of heart 26 may be used to control the timing of the delivery of pacing, cardioversion or defibrillation shocks by therapy module 46. For example, processor 46 may employ any suitable arrhythmia detection methodologies in order to detect an arrhythmia based on electrical cardiac signals sensed by sensing module 48, and the detection of an arrhythmia may be used to control the delivery of defibrillation shocks by therapy module 46, e.g., to attempt to terminate the detected arrhythmia.

Modules 46, 48 may be electrically coupled to one or more electrodes of the respective lead 18, 20 and 22 via conductors of the respective lead, or, in the case of a housing electrode, via an electrical conductor disposed within housing 28 of IMD 14. In some examples, therapy module 46 may deliver defibrillation shocks to heart 26 via at least two electrodes coupled to leads 18, 20, 22, connector assembly 40 or housing 28. Therapy module 46 may deliver pacing pulses via the housing electrode, ring electrodes coupled to leads 18, 20, 22, respectively, and/or helical electrodes of leads 18, 20, 22. In some examples, therapy module 46 may deliver pacing, cardioversion, or defibrillation stimulation in the form of electrical pulses.

Module 46, 48 may include a switch module, and processor 45 may use the switch module to select, e.g., via a data/address bus, which of the available electrodes of housing 28 and leads 16, 42 are used to deliver electrical stimulation. The switch module may include a switch array, switch matrix, multiplexer, or any other type of switching device suitable to selectively couple stimulation energy to selected electrodes. In other examples, however, module 46, 48 may independently deliver stimulation and/or sensing via the electrodes without a switch matrix.

In some examples modules 46, 48 may share one or more components utilized to operate as described herein. For example, in some cases, therapy module 46 and sensing module 48 may share a switch module. In addition, in some examples, modules 46, 48 may include components dedicated to only a single module. For example, modules 46, 48, respectively, may have respective processors and/or memories.

Telemetry module 52 includes any suitable hardware, firmware, software or any combination thereof for communicating with another device, such as programmer 24 (FIG. 1). Under control of processor 45 of IMD 14, telemetry module 52 may receive downlink telemetry from and send uplink telemetry to programmer 24 with the aid of an antenna, which may be internal and/or external. IMD 14 may provide the data to be uplinked to programmer 24 and the control signals for the telemetry circuit within telemetry module 52 e.g., via an address/data bus. In some examples, telemetry module 52 may provide received data to a processor of IMD 14 via a multiplexer.

The various components of IMD 14 may be coupled to power supply 50, which may include a rechargeable or non-rechargeable battery. A non-rechargeable battery may be selected to last for several years, while a rechargeable battery may be inductively charged from an external device, e.g., on a daily or weekly basis. In other examples, power supply 50 may be powered by proximal inductive interaction with an external power supply carried by patient 12.

As previously described, IMD 14 may be mechanically coupled to leads 18, 20 and 22, and electrically coupled to electrodes of leads 18, 20 and 22 via lead connector assembly 40. Although FIG. 2 illustrates a lead connector assembly configured to receive three leads, in other examples, lead connector modules or assemblies described herein may include any suitable number of electrical connectors to electrically couple any suitable number of leads to therapy module 46 and sensing module 48. Accordingly, in some examples, lead connector assembly 40 may include additional electrical connectors that are configured to receive additional leads of system 10.

Electrical connectors 54, 55, 56 within connection assembly 40 may be any suitable type of electrical connector capable of electrically and mechanically coupling leads 18, 20 and 22, respectively, to IMD 14. For example, electrical connectors 54, 55, 56 may each be configured as receptacles configured to receive a proximal end of the respective leads 18, 20, 22 (or a lead extension). In some examples, the proximal end of a lead (or lead extension) may be physically secured in the corresponding electrical connector receptacle via a set screw, while in other examples, the proximal end of each lead (or lead extension) may mate with the receptacle in a self-securing manner. In some examples, connectors 54, 55, 56 are Bayonet Neill Concelman (BNC) electrical connectors or have configurations similar to BNC electrical connectors, which are physically configured to mate with the respective leads 18, 20, 22, 16. In addition, in some examples, connectors 54, 55, 56 are threaded Neill Concelman (TNC) type electrical connectors or have configurations (e.g., bayonet mount style) similar to TNC electrical connectors, which are configured to physically mate with and receive leads 18, 20 and 22 in a threaded configuration. In other examples, connectors 54, 55, 56 are connected to leads 42, 16 without the aid of a set screw, such as with the aid of a lever that pushes leads 18, 20 and 22 into physical and electrical connection with electrical contacts within the respective electrical connectors 54, 55, 56.

FIGS. 3A-3B illustrate an IMD 100. IMD 100 includes housing 150, medical lead connector assembly 110 and preformed gasket 140. IMD 100 is suitable for implantation within a patient. For example, lead connector assembly 110 includes suture openings 119, which may aid in securing IMD 100 inside the body of a patient. In some examples, an IMD housing may also include one or more suture openings to aid in securing an IMD within a patient. As implanted within a patient, IMD 100 is suitable for delivering a medical therapy such as electrical stimulation therapy and/or sensing one or more physiological conditions of a patient. As an example, IMD 100 may provide some or all of the features described with respect to IMD 14.

Housing 150 is formed from a biocompatible conductive material, such as a titanium alloy or stainless steel. For example, housing 150 may be formed from two mating clam shells in an overlapping or butt welded construction. Housing 150 may be hermetically sealed, e.g., by laser or resistance welding, to form an enclosure. Housing 150 encloses therapy module configured to generate an electrical stimulation therapy and/or a sensing module to sense one or more physiological conditions for a patient, as well as a power supply and a telemetry module. Feedthroughs 154 extend through housing 150 and provide an electrical connection to the therapy module within housing 150.

Brackets 152 are secured to an exterior surface of housing 150. While brackets 152 are depicted as L-shaped brackets, other configurations are also suitable. As an example, brackets 152 may be formed from the same or a similar biocompatible conductive material as housing 150 and welded to housing 150. As another example, brackets 152 may be molded as integral features of housing 150. Brackets 152 extend from housing 150 in a common direction toward lead connector assembly 110, the common direction being about perpendicular to the external surface of housing 150. Each of brackets 152 includes a hole for receiving a corresponding pin 160 to mechanically secure lead connector assembly 110 to housing 150. Brackets 152 are positioned adjacent three corners of upper surface 155 of housing 150. Feedthroughs 154 are located adjacent the fourth corner of upper surface 155 of housing 150, which precludes the addition of an additional bracket at that corner. Brackets 152 are positioned adjacent the corners of upper surface 155 of housing 150 to provide stability for lead connector assembly 110 as mounted to housing 150 and provides a balanced sealing force from preformed gasket 140 about the interface of housing 150 and lead connector assembly 110. In other examples, an IMD similarly configured to IMD 100 may include more or less brackets. As an example, an IMD housing may include four brackets with one bracket positioned adjacent each corner of a housing surface that sits adjacent a lead connector assembly in an assembled IMD.

Figure 4:
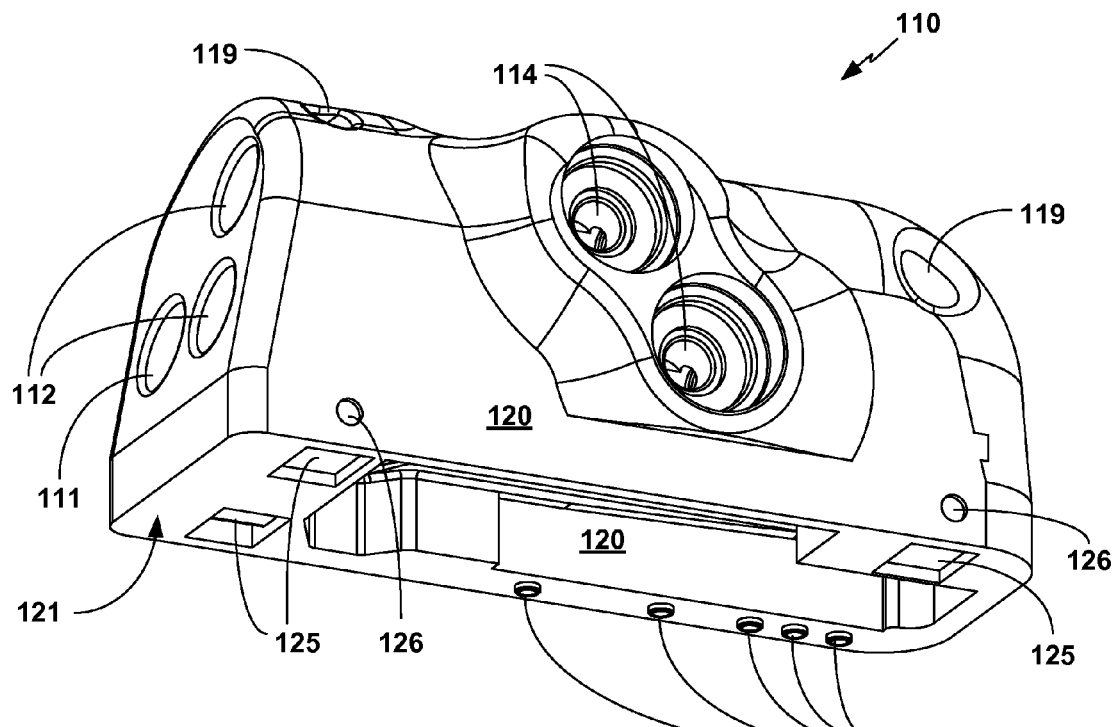
FIG. 4 illustrates the medical lead connector assembly of the IMD shown in FIGS. 3A-3B.
Figure 6:
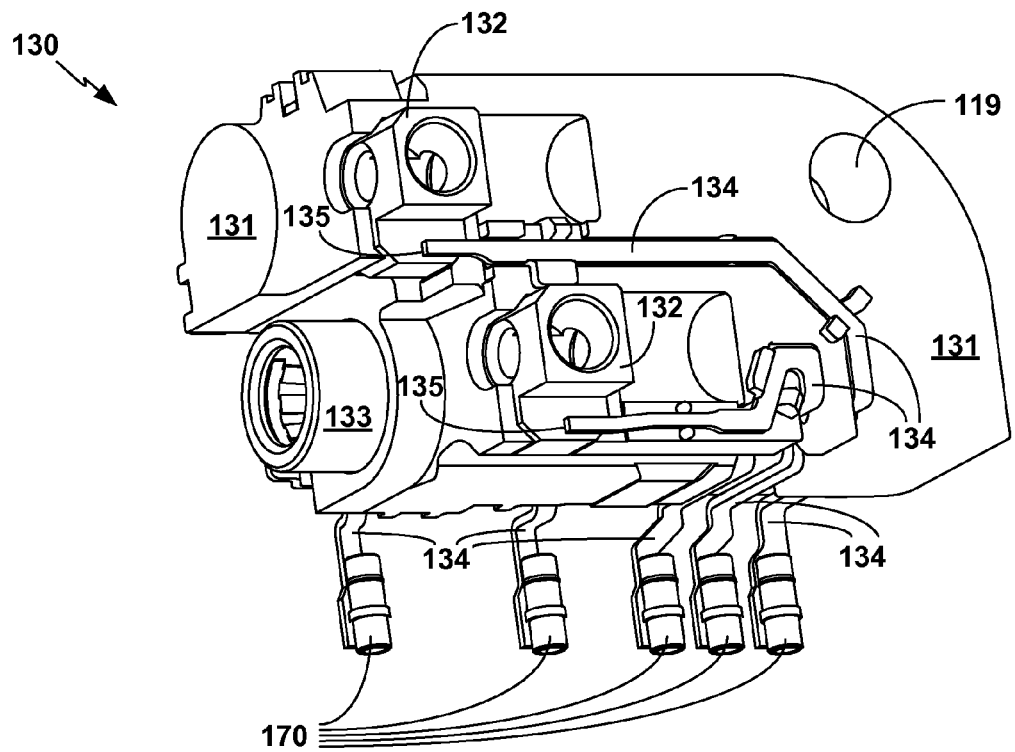
FIG. 6 illustrates a primary molding and the internal conductors of the medical lead connector assembly of FIG. 4.

FIG. 4 illustrates medical lead connector assembly 110 of 100. FIG. 6 illustrates primary molding 130 with internal conductors 134 of the medical lead connector assembly of FIG. 4. In particular, FIG. 6 represents an intermediate stage in a manufacturing process of lead connector assembly 110. The final shape of medical lead connector assembly 110 including lead connector assembly body 120, e.g., as shown in FIG. 4, may be formed by applying an overmold to primary molding 130. Lead connector assembly body 120 and primary molding body 131 are formed from biocompatible polymers. Examples of biocompatible polymers suitable for lead connector assembly body 120 and primary molding body 131 include thermo plastic polymers including but not limited to polyurethane and PEEK or thermoset polymers such as epoxy, silicone or other thermoset resins.

Lead connector assembly 110 includes solderless connectors 170, which are configured to form electrical connections with feedthroughs 154 when lead connector assembly 110 is mounted to housing 150. Internal conductors 134 provide electrical connections between solderless connectors 170 and connector blocks 132, 133. Internal conductors 134 pass within lead connector assembly body 120 and are welded to solderless connectors 170 as well as to connector blocks 132, 133. For example, internal conductors 134 may spot welded to connector blocks 132 at contact points 135 (FIG. 6). In lead connector assembly 110, each feedthrough 154 is electrically connected to a single connector block, but in other examples, one feedthrough could be electrically connected to more than one connector block, e.g., a feedthrough providing a ground voltage could connect to multiple connector blocks.

Connector blocks 132, 133 are configured to form electrical connections with medical leads inserted in electrical connectors 111, 112. Electrical connectors 111, 112 each define an opening configured to receive a medical lead. Electrical connector 111 includes connector block 133 as well as a second connector block (not shown), whereas electrical connectors 112 each include only a single connector block 132. Connectors blocks 132 are each configured to receive a set screw (not shown) in the corresponding screw hole 114 to secure a medical lead inserted in the corresponding electrical connector. The set screws contact a proximal portion of the medical leads and promote electrical contact between a lead conductor and the connector block. In addition to connector block 133, electrical connector 111 includes a second connector block (not shown), which is configured to receive a set screw. While lead connector assembly 110 is shown as having three electrical connectors 111, 112, a lead connector assembly within the spirit of this disclosure could include any number of electrical connectors that define an opening configured to receive a medical lead, including, e.g., one, two, three or four electrical connectors.

Lead connector assembly 110 includes many features which facilitate mounting lead connector assembly 110 to housing 150. As one example, solderless connectors 170 protrude from the bottom surface 121 of lead connector assembly 110 in order to receive feedthroughs 154 when lead connector assembly 110 is mounted to housing 150. In addition, lead connector assembly 110 includes bracket recesses 125. Bracket recesses 125 are configured to align with brackets 152 and bracket apertures 145 of preformed gasket 140 when lead connector assembly 110 is mounted to housing 150. As another example, body 120 of lead connector assembly 110 includes pin alignment indents 126. As discussed in further detail below, pin alignment indents 126 are configured to align pins 160 (FIG. 3A) with holes in brackets 152 during assembly of IMD 100. Generally, pins 160 may comprise a biocompatible metal material, such as a titanium alloy or stainless steel. In other examples, pins 160 may comprise a biocompatible polymer material.

Figure 5:
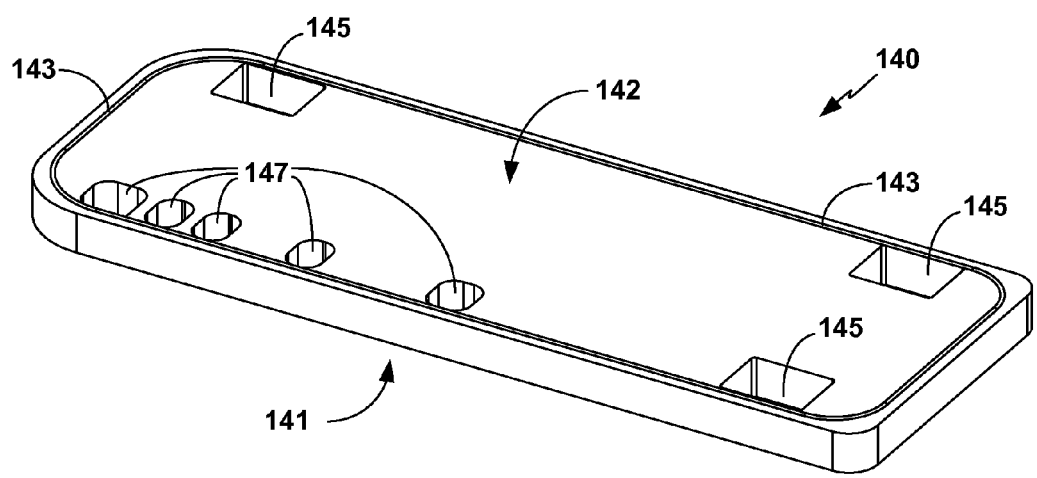
FIG. 5 illustrates the preformed gasket of the IMD shown in FIGS. 3A-3B

FIG. 5 illustrates preformed gasket 140. Preformed gasket 140 is configured to fit between housing 150 and medical lead connector assembly 110 in IMD 100. When implanted within a patient, the environment external to IMD 100 will generally include bodily fluids, which can cause shorts between feedthroughs 154 and/or current leakage into the body of the patient. Preformed gasket 140 provides a means for electrically isolating feedthroughs 154 from each other and from an environment external to IMD 100 without using a wet adhesive or back filling, such as back filling using a polymeric material.

Preformed gasket 140 includes an approximately flat bottom surface 141, which is configured to match the contour of upper surface 155 of housing 150. Similarly, preformed gasket 140 also includes an approximately flat upper surface 142, which is configured to match the contour of bottom surface 121 of lead connector assembly 110. In other examples, the surfaces of preformed gasket 140 may be of different shapes, but still be configured to provide sealing between feedthroughs 154. Preformed gasket 140 includes bracket apertures 145, which are configured to align with brackets 152 on housing 150 as well as feedthrough apertures 147, which are configured to align with feedthroughs 154 on housing 150. With the exception of apertures 145, 147, preformed gasket 140 has a substantially prismatic polyhedron shape. In other examples, a preformed gasket may have a single aperture configured to enclose all of feedthroughs 154, which would still provide a seal to electrically isolate feedthroughs 154 from each other when IMD 200 is implanted within a patient. However, having separate feedthrough apertures 147 for each of feedthroughs 154 may maintain electrical isolation of feedthroughs 154 even if there is fluidic contamination within one or more of feedthrough apertures 147.

Preformed gasket 140 includes projection 143, which is located about the perimeter of gasket 140. In IMD 100, projection 143 faces lead connector assembly 110 and functions to concentrate the sealing force between gasket 140 and lead connector assembly 110 at projection 143, i.e., about the perimeter of gasket 140. In this manner, projection 143 may improve the reliability of the sealing provided by gasket 140. In some examples, preformed gasket 140 may include additional or different projections to concentrate sealing forces where desired. For example, a projection could be located about the perimeter of gasket 140 facing housing 150. As another example, one or more projections could surround feedthroughs 154. Alternatively or in combination with projections on preformed gasket 140, upper surface 155 of housing 150 and/or bottom surface 121 of lead connector assembly 110 may also include projections to concentrate sealing forces. Further, upper surface 155 of housing 150 and/or bottom surface 121 of lead connector assembly could also form one more depressions configured to mate with a corresponding projection on preformed gasket 140. Such depressions may assist in ensuring proper alignment between preformed gasket 140, lead connector assembly 110 and/or housing 150. In different examples, preformed gasket 140 may be formed using a mold, with a machining or cutting operation or using a combination of manufacturing techniques.

In some examples, preformed gasket 140 may be bonded to lead connector assembly 110 such that lead connector assembly 110 and preformed gasket 140 serve as a unitary component during the assembly of IMD 100. This may help ensure proper alignment of lead connector assembly 110 and preformed gasket 140 as well as proper alignment of preformed gasket 140 and housing 150 during the assembly of IMD 100. As another example, preformed gasket 140 may be bonded to housing 150 such that housing 150 and preformed gasket 140 serve as a unitary component during the assembly of IMD 100 to help ensure proper alignment of preformed gasket 140 in IMD 100. As an example, preformed gasket 140 may be bonded to lead connector assembly 110 or housing 150 using an adhesive, such as a silicon-based adhesive. As another example, preformed gasket 140 may be bonded to lead connector assembly 110 or housing 150 by overmolding preformed gasket 140 directly onto bottom surface 121 of lead connector assembly 110 or upper surface 155 of housing 150.

During the assembly of IMD 100, preformed gasket 140 is compressed between housing 150 and lead connector assembly 110 to electrically isolate feedthroughs 154 from each other. As one example, preformed gasket 140 may be compressed between housing 150 and lead connector assembly 110 during the assembly of IMD 100 such that preformed gasket 140 experiences elastic deformation in forming a seal. In such an example, preformed gasket 140 may be formed a molded silicon material although other materials may also be used. Alternatively, preformed gasket 140 may experience a degree of inelastic deformation when compressed between housing 150 and lead connector assembly 110 during the assembly of IMD 100. In such an example, preformed gasket 140 may be formed a polyether resin although other materials may also be used. Examples of suitable polyether resins include Tecothane® resins, which are available from Lubrizol Corporation of Wickliffe, Ohio, United States.

Figure 7A:
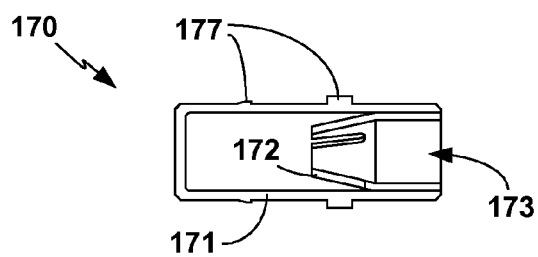
FIGS. 7A-7D illustrate a solderless connector used in the medical lead connector assembly of FIG. 4.
Figure 7B:
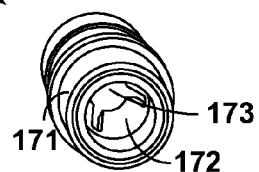
Figure 7C:
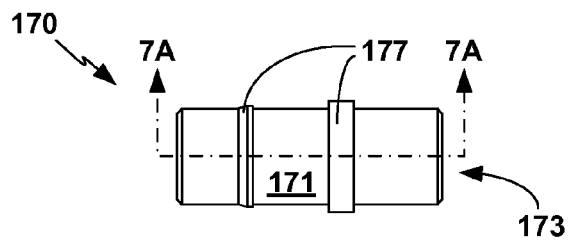
Figure 7D:
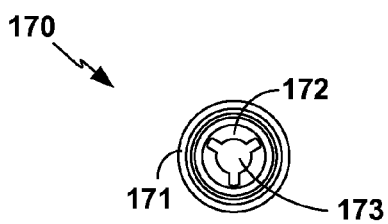

FIGS. 7A-7D illustrate an example configuration of a solderless connector 170. Specifically, FIG. 7A illustrates a cutaway view of solderless connector 170, FIG. 7B illustrates an orthogonal view of solderless connector 170, FIG. 7C illustrates a side view of solderless connector 170, and FIG. 7D illustrates a front view of solderless connector 170. As best as shown in FIG. 6, lead connector assembly 110 includes five solderless connectors 170.

Solderless connector 170 includes cylindrical housing 171, which forms central aperture 173. Spring member 172 is located within cylindrical housing 171 and forms a portion of central aperture 173. Both cylindrical housing 171 and spring member 172 are electrically conductive. Central aperture 173 and spring member 172 are configured to receive one of feedthroughs 154 during the assembly of IMD 100. For example spring member 172 is configured to deform to receive a corresponding feedthrough 154 within central aperture 173 and provide a reliable electrical connection with the corresponding feedthrough 154.

Solderless connector 170 also includes outer radial protrusions 177. Outer radial protrusions 177 function to register solderless connectors 170 on internal conductors 134 during a welding process to mechanically and electrically connect solderless connectors 170 to internal conductors 134. In addition, radial protrusions 177 also serve to secure solderless connectors 170 within lead connector assembly body 120 (FIG. 4) by providing an irregular exterior surface on cylindrical housing 171 which is encased within lead connector assembly body 120 during a molding process.

During the assembly of IMD 100, bottom surface 121 of lead connector assembly 110 is positioned in alignment with upper surface 155 of housing 150. Concurrently, preformed gasket 140 is positioned between bottom surface 121 of lead connector assembly 110 and upper surface 155 of housing 150. With housing 150, preformed gasket 140 and lead connector assembly 110 in proper alignment, lead connector assembly 110 is pressed onto housing 150 such that feedthroughs 154 enter central apertures 173 of solderless connectors 170 and form electrical connections with solderless connectors 170. Lead connector assembly 110 is pressed with sufficient force to compress preformed gasket 140 between housing 150 and lead connector assembly 110. Compressing preformed gasket 140 forms a seal that electrically isolates feedthroughs 154 from each other and from an external environment. Then, while maintaining the compressive force on preformed gasket 140, lead connector assembly 110 is mechanically secured to housing 150 using pins 160. Specifically, pins 160 are aligned with pin alignment indents 126 and pressed into body 120 of lead connector assembly 110. Pin alignment indents 126 align with the holes in brackets 152 such that pins 160 pass through the holes in brackets 152. Body 120 of lead connector assembly 110 deforms to receive pins 160, and pins remain securely embedded within body 120. Once lead connector assembly 110 is mechanically secured to housing 150 using pins 160, the compressive force applied to housing 150 and lead connector assembly 110 during the assembly process may be released. Pins 160 then hold lead connector assembly 110 in place to maintain compression on preformed gasket 140 and also to maintain the seal provided by preformed gasket 140. In this manner, preformed gasket 140 provides a means for electrically isolating feedthroughs 154 from each other and from an external environment without the need for backfilling or a wet adhesive during the assembly of housing 150 and lead connector assembly 110.

FIGS. 8A-8B illustrate IMD 200. IMD 200 is substantially similar to IMD 100 except that IMD 200 uses an alternative technique for mechanically securing a lead connector assembly to an IMD housing. For brevity, features of IMD 200 that are the same or similar to features discussed with respect to IMD 100 are discussed in limited detail with respect to IMD 200. Like IMD 100, IMD 200 includes housing 150 and preformed gasket 140. IMD 200 further includes medical lead connector assembly 210, which contrasts lead connector assembly 110 of IMD 100. IMD 200 is suitable for implantation within a patient. For example, lead connector assembly 210 includes suture openings 219, which may aid in securing IMD 200 inside the body of a patient. As implanted within a patient, IMD 200 is suitable for delivering a medical therapy such as electrical stimulation therapy and/or sensing one or more physiological conditions of a patient. As an example, IMD 200 may provide some or all of the features described with respect to IMD 14.

Lead connector assembly 210 includes electrical connectors 212. Electrical connectors 212 each define an opening configured to receive a medical lead. Such medical leads can be secured to electrical connectors 212 using set screws, such as a set screw threaded into screw hole 214.

As best illustrated by the close-up cut away view of FIG. 8B, lead connector assembly 210 is configured to "snap-on" to housing 150. Lead connector assembly 210 includes a set of slots, as represented by slot 234 in FIG. 8B, to receive brackets 152. With each of these slots, lead connector assembly 210 includes a metal snap-on tab, one of which is shown as snap-on tab 232 in FIG. 8B. Each snap-on tab is angled to bend and slide over the corresponding bracket 152 when lead connector assembly 210 is pressed onto housing 150. Once lead connector assembly 210 is pressed far enough onto housing 150, the snap-on tabs snap into place and mate with the hole of the corresponding brackets 152. In this manner, the snap-on tabs mechanically secure lead connector assembly 210 to housing 150. With the snap-on tabs mated to the holes in brackets 152, preformed gasket 140 remains compressed between housing 150 and lead connector assembly 210, and preformed gasket 140 forms a seal that electrically isolates feedthroughs 154 from each other and from an external environment. The snap-on configuration of lead connector assembly 210 may provide for easier assembly than with lead connector assembly 110.

The lead connector assemblies described herein are merely examples of the disclosure and the disclosure is not limited to such configurations. Instead, in some examples, any suitable electrical connectors known in the art may be utilized. Furthermore, examples of the present disclosure may not be limited to therapy systems configured to deliver one or two different types of stimulation therapy to a patient. In some examples, an IMD may include two or more therapy modules configured to deliver different types of stimulation therapies to a patient. In such cases, a lead connector assembly may include two or more electrical connectors that correspond to each therapy module. Alternatively, an IMD may include multiple lead connector assemblies corresponding to different therapy modules within the IMD. In other example, an IMD may include a single therapy module configured to deliver stimulation therapy to a patient via two or more lead connector assemblies.

In general, configuration of the electrical connectors of lead connector assemblies described herein may be modified to be consistent with the type of lead being used to deliver electrical stimulation therapy to a patient from IMD and still be within the scope of the disclosure. For example, a number of electrical contacts of an electrical connector may correspond to the number of electrical contacts of a lead that is electrically connected to the electrical connector.

While, IMDs 14, 100, 200 are generally described as delivering cardiac therapy such as pacing, cardioversion, defibrillation or cardiac resynchronization therapy, IMDs configured for delivering other therapies may also incorporate a preformed gasket between a lead connector assembly and an IMD housing to isolate electrical connections between the lead connector assembly and the IMD housing from an external environment in accordance with the techniques disclosed herein. For example, such IMDs may be configured to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. Such IMDs may include an electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

Further, while IMDs 14, 100, 200 are described as including lead connector assemblies 40, 110, 210 respectively, IMDs with header assemblies that do no include electrical connectors configured to receive a proximal end of a medical lead may also incorporate a preformed gasket between the header assembly and a housing of the IMD in accordance with the techniques disclosed herein. As an example, such header assemblies may include an antenna, such as telemetry coil, an inductive powering coil. As another example, such header assemblies may include one or more header assembly electrodes for sensing and/or stimulation and/or include one or more sensors such as pressure sensors or temperature sensors. Such IMDs may incorporate a preformed gasket between a header assembly and an IMD housing to isolate electrical connections between the header assembly and the IMD housing from an external environment in accordance with the techniques disclosed herein.

In addition, embodiments of the invention may be practiced with IMDs incorporating a drug pump, wherein drug delivery catheters may be equivalent to leads, such as the leads of system 10. In such examples, a drug delivery port and or refill port at the interface of an IMD housing and an IMD header assembly may be isolated from an external environment using a preformed gasket between the header assembly and the housing in accordance with the techniques disclosed herein.

The techniques described in this disclosure, including those attributed to IMD 14, programmer 24, IMD 100 and IMD 200, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described herein. These and other examples are within the scope of the following claims.

The invention claimed is:

1. An implantable medical device comprising:
a housing;
a module enclosed within the housing and configured to at least one of generate an electrical stimulation therapy for delivery to a patient or monitor a physiological parameter of the patient;
a plurality of feedthroughs extending through the housing;
a header assembly including one or more electrical connectors electrically coupled to the module via the feedthroughs;
one or more compression-fit connectors electrically coupling the feedthroughs to the electrical connectors, wherein each of the compression-fit connectors comprises an electrically conductive spring member forming a central aperture, the spring member deformed to receive a corresponding feedthrough in its central aperture and form an electrical connection with the corresponding feedthrough;
a preformed gasket compressed between the housing and the header assembly forming a seal to electrically isolate the feedthroughs from each other and from an external environment; and
a set of brackets secured to the housing and extending into the header assembly,
wherein the header assembly further includes a set of slots configured to mate with the set of brackets,
wherein the header assembly further includes a snap-on tab within each of the set of slots, and
wherein each snap-on tab is configured to bend and slide past at least a portion of a corresponding bracket and is configured to mate with the corresponding bracket.

2. The implantable medical device of claim 1, wherein the preformed gasket is elastically deformed as compressed between the housing and the header assembly.

3. The implantable medical device of claim 1, wherein the preformed gasket comprises a silicon material.

4. The implantable medical device of claim 1, wherein the preformed gasket comprises a polyether resin.

5. The implantable medical device of claim 1, wherein the preformed gasket is bonded to the header assembly such that the header assembly and the preformed gasket serve as a unitary component.

6. The implantable medical device of claim 1, wherein the preformed gasket includes a plurality of apertures corresponding to the feedthroughs, wherein each feedthrough extends through a different one of the apertures.

7. The implantable medical device of claim 1, wherein the header assembly is a lead connector assembly.

8. The implantable medical device of claim 1,
wherein the preformed gasket compressed between the housing and the header assembly electrically isolates the feedthroughs from each other and from the external environment without the need for backfilling or a wet adhesive during the assembly of the housing and the header assembly.

9. The implantable medical device of claim 1,
wherein the feedthroughs extend from the housing in a generally perpendicular direction relative to the housing,
wherein the central apertures of the plurality of compression-fit connectors electrically coupling the feedthroughs to the electrical connectors receive the feedthroughs in the generally perpendicular direction relative to the housing, and
wherein the preformed gasket is compressed between the housing and the header assembly in the generally perpendicular direction.

10. The implantable medical device of claim 9, wherein the plurality of compression-fit connectors each include a cylindrical housing forming the central aperture with the central aperture being coincident with a central axis of the cylindrical housing.

11. An implantable medical device, comprising:
a housing;
a module enclosed within the housing and configured to at least one of generate an electrical stimulation therapy for delivery to a patient or monitor a physiological parameter of the patient;
a plurality of feedthroughs extending through the housing;
a header assembly including one or more electrical connectors electrically coupled to the module via the feedthroughs;
one or more compression-fit connectors electrically coupling the feedthroughs to the electrical connectors, wherein each of the compression-fit connectors comprises an electrically conductive spring member forming a central aperture, the spring member deformed to receive a corresponding feedthrough in its central aperture and form an electrical connection with the corresponding feedthrough; and
a preformed gasket compressed between the housing and the header assembly forming a seal to electrically isolate the feedthroughs from each other and from an external environment,
wherein the preformed gasket, when in a non-compressed state, includes a projection around a perimeter of the gasket, the projection facing the header assembly and functioning to concentrate sealing force between the gasket and the header assembly at the perimeter of the gasket.

12. The implantable medical device of claim 11, further comprising:
a set of brackets secured to the housing and extending into the header assembly; and
a set of pins extending through the brackets and into the header assembly to secure the header assembly to the housing at a position that compresses the preformed gasket between the housing and the header assembly.

13. The implantable medical device of claim 12, wherein the preformed gasket includes a set of apertures corresponding to the brackets, wherein each bracket extends through a different one of the apertures.

14. The implantable medical device of claim 11, further comprising a set of brackets secured to the housing and extending into the header assembly,
wherein the header assembly includes a set of slots configured to mate with the set of brackets,
wherein the header assembly further includes a snap-on tab within each of the set of slots, and
wherein each snap-on tab mates with a corresponding bracket to mechanically secure the header assembly to the housing.

15. The implantable medical device of claim 11, wherein the header assembly comprises a lead connector assembly, wherein the electrical connectors each include one or more connector blocks, wherein the electrical connectors each define an opening configured to receive a medical lead.

16. The implantable medical device of claim 11, further comprising means for mechanically securing the header assembly to the housing.

17. A method of manufacturing an implantable medical device, the implantable medical device comprising:
    a subassembly including: a substantially sealed housing, a module enclosed within the housing and configured to at least one of generate an electrical stimulation therapy for delivery to a patient or monitor a physiological parameter of the patient, a plurality of feedthroughs extending through the housing, and a set of brackets secured to the housing;
    a header assembly including one or more electrical connectors, a set of slots configured to mate with the set of brackets, and a snap-on tab within each of the set of slots; and
    a preformed gasket configured to electrically isolate the feedthroughs from each other and from an external environment when the header assembly is mounted to the substantially sealed housing,
    wherein the method comprises:
    positioning the preformed gasket between the header assembly and the housing;
    positioning the header assembly on the housing and pressing the header assembly on to the housing to form a plurality of electrical connections with a plurality of compression-fit connectors between the feedthroughs and the electrical connectors and compress the preformed gasket between the header assembly and the housing to form a seal that electrically isolates the feedthroughs from each other and the external environment,
    wherein each of the compression-fit connectors comprises an electrically conductive spring member forming a central aperture, the spring member deformed to receive a corresponding feedthrough in its central aperture and form an electrical connection with the corresponding feedthrough; and
    wherein pressing the header assembly onto the housing comprises pressing the header assembly onto the housing until each snap-on tab bends and slides past at least a portion of a corresponding bracket and mates with the corresponding bracket to mechanically secure the header assembly to the housing and to maintain the seal provided by the preformed gasket.

18. The method of claim 17, wherein the preformed gasket is elastically deformed as compressed between the housing and the header assembly.

19. The method of claim 17, wherein the preformed gasket comprises a silicon material.

20. The method of claim 17, wherein the preformed gasket comprises a polyether resin.

21. The method of claim 17, wherein the preformed gasket is bonded to the header assembly such that the header assembly and the preformed gasket serve as a unitary component.

22. The method of claim 17, wherein the preformed gasket includes a plurality of apertures corresponding to the feedthroughs, wherein each feedthrough extends through a different one of the apertures once the header assembly is secured to the housing.

23. The method of claim 17, wherein the header assembly is a lead connector assembly.

24. The method of claim 23, wherein the electrical connectors each include one or more connector blocks, wherein the electrical connectors each define an opening configured to receive a medical lead.

25. The method of claim 17, wherein positioning the header assembly on the housing to compress the preformed gasket between the header assembly and the housing electrically isolates the feedthroughs from each other and from the external environment without the need for backfilling or a wet adhesive during the assembly of the housing and the header assembly.

26. The method of claim 17,
    wherein the feedthroughs extend from the housing in a generally perpendicular direction relative to the housing, and
    wherein positioning the header assembly on the housing to form the plurality of electrical connections with the plurality of compression-fit connectors between the feedthroughs and the electrical connectors and compress the preformed gasket between the header assembly and the housing to form a seal that electrically isolates the feedthroughs from each other and from the external environment comprises positioning the header assembly on the housing in the generally perpendicular direction to simultaneously insert the feedthroughs into the respective central apertures of the compressive-fit connectors to form the plurality of electrical connections with the plurality of compression-fit connectors and press the preformed gasket between the header assembly and the housing.

27. A method of manufacturing an implantable medical device, the implantable medical device comprising:
    a subassembly including: a substantially sealed housing, a module enclosed within the housing and configured to at least one of generate an electrical stimulation therapy for delivery to a patient or monitor a physiological parameter of the patient, and a plurality of feedthroughs extending through the housing;
    a header assembly including one or more electrical connectors; and
    a preformed gasket configured to electrically isolate the feedthroughs from each other and from an external environment when the header assembly is mounted to the substantially sealed housing, wherein the preformed gasket, when in a non-compressed state, includes a projection around a perimeter of the gasket, the projection facing the header assembly and functioning to concentrate sealing force between the gasket and the header assembly at the perimeter of the gasket,
    wherein the method comprises:
    positioning the preformed gasket between the header assembly and the housing;
    positioning the header assembly on the housing to form a plurality of electrical connections with a plurality of compression-fit connectors between the feedthroughs and the electrical connectors and compress the preformed gasket between the header assembly and the housing to form a seal that electrically isolates the feedthroughs from each other and the external environment,
    wherein each of the compression-fit connectors comprises an electrically conductive spring member forming a central aperture, the spring member deformed to receive a corresponding feedthrough in its central aperture and form an electrical connection with the corresponding feedthrough; and
    mechanically securing the header assembly to the housing to maintain the seal provided by the preformed gasket.

28. An implantable medical device comprising:
a housing;
a module enclosed within the housing and configured to at least one of generate an electrical stimulation therapy for delivery to a patient or monitor a physiological parameter of the patient;
a plurality of feedthroughs extending through the housing;
a header assembly including an electrical connector electrically coupled to the module via the feedthroughs;
a plurality of compression-fit connectors electrically coupling the feedthroughs to the electrical connectors, wherein each of the compression-fit connectors comprises an electrically conductive spring member forming a central aperture, the spring member deformed to receive a corresponding feedthrough in its central aperture and form an electrical connection with the corresponding feedthrough;
means for electrically isolating the feedthroughs from each other and from an external environment; and
a set of brackets secured to the housing and extending into the header assembly,
wherein the header assembly further includes a set of slots configured to mate with the set of brackets,
wherein the header assembly further includes a snap-on tab within each of the set of slots, and
wherein each snap-on tab is configured to bend and slide past at least a portion of a corresponding bracket and is configured to mate with the corresponding bracket.

29. The implantable medical device of claim 28,
wherein the means for electrically isolating the feedthroughs from each other and from the external environment comprises means for electrically isolating the feedthroughs from each other and from the external environment without the need for backfilling or a wet adhesive during the assembly of the housing and the header assembly.

30. The implantable medical device of claim 28,
wherein the feedthroughs extend from the housing in a generally perpendicular direction relative to the housing,
wherein the central apertures of the plurality of compression-fit connectors electrically coupling the feedthroughs to the electrical connectors receive the feedthroughs in the generally perpendicular direction relative to the housing, and
wherein the preformed gasket is compressed between the housing and the header assembly in the generally perpendicular direction.

* * * * *